(12) United States Patent
Morris et al.

(10) Patent No.: US 7,091,004 B1
(45) Date of Patent: Aug. 15, 2006

(54) REGULATION OF TRANSLATION FOR RECOMBINANT PROTEIN PRODUCTION

(75) Inventors: Arvia E. Morris, Seattle, WA (US); Sharon T. Wong-Madden, Bellevue, WA (US)

(73) Assignee: Immunex Corporation, Seattle, WA (US)

( * ) Notice: Subject to any disclaimer, the term of this patent is extended or adjusted under 35 U.S.C. 154(b) by 218 days.

(21) Appl. No.: 10/165,591

(22) Filed: Jun. 7, 2002

Related U.S. Application Data

(60) Provisional application No. 60/297,153, filed on Jun. 8, 2001.

(51) Int. Cl.
*C12P 21/06* (2006.01)
*C12N 5/00* (2006.01)
*C12N 15/63* (2006.01)

(52) U.S. Cl. .................. 435/69.1; 435/325; 435/358; 435/359; 435/360; 435/361; 435/455

(58) Field of Classification Search .............. 435/41, 435/69.1, 70.1, 70.3, 440, 455, 325
See application file for complete search history.

(56) References Cited

U.S. PATENT DOCUMENTS

| 5,858,753 A * | 1/1999 | Chantry et al. ............. 435/194 |
| 6,413,744 B1 | 7/2002 | Morris et al. .............. 435/69.1 |
| 2003/0040047 A1 | 2/2003 | Farwick et al. ............ 435/69.1 |

FOREIGN PATENT DOCUMENTS

| WO | WO 00/68400 | 11/2000 |

OTHER PUBLICATIONS

Hara et al. Regulation of elF-4E BPI Phosphorylation by mTOR*. J. Biol. Chem. 272:26457-26463, 1997.*
Aoki et al., "A role of the kinase mTOR in cellular transformation induced by the oncoproteins P3k and Akt," *PNAS* 98(1):136-141, Jan. 2, 2001.
Dufner et al., "Protein Kinase B Localization and Activation Differentially Affect S6 Kinase 1 Activity and Eukaryotic Translation Initiation Factor 4E-Binding Protein 1 Phosphorylation," *Mol and Cell Biol* 19(6):4525-4534, Jun. 1999.
Gingras et al., "4E-BP1, a repressor of mRNA translation, is phosphorylated and inactivated by the Akt(PKB) signaling pathway," *Genes and Development* 12:502-513, 1998.
Robbins and Horlick, "Macrophage Scavenger Receptor Confers Adherent Phenotype to Cells in Culture," *BioTechniques* 25(2):240-244, 1998.
Stambolic et al., "Modulation of cellular apoptotic potential: contributions to oncogenesis," *Oncogene* 18:6094-6103, 1999.
Vanhaesebroeck and Alessi, "The P13K-PDK1 connection: more than just a road to PKB," *Biochem J* 346:561-576, 2000.

* cited by examiner

*Primary Examiner*—Nancy Vogel
*Assistant Examiner*—Walter Schlapkohl
(74) *Attorney, Agent, or Firm*—Kathleen Fowler

(57) ABSTRACT

The invention provides cells that produce increased levels of recombinant protein by modulating the activity of translational regulator gene products that are downstream targets of PKB alpha, methods of making such cells, and methods of using such cells. Such translational regulator gene products include 4E-BP1 and mTOR.

14 Claims, 2 Drawing Sheets

REGULATION OF TRANSLATION FOR RECOMBINANT PROTEIN PRODUCTION

RELATED APPLICATION DATA

This application claims the benefit of U.S. Provisional Application No. 60/297,153, filed Jun. 8, 2001, the disclosure of which is incorporated by reference herein.

FIELD OF THE INVENTION

The invention is in the field of protein production, particularly recombinant protein production in cell culture.

BACKGROUND

When a hormone such as insulin binds to its cell surface tyrosine kinase receptor, a cellular kinase cascade occurs which leads to the activation of phosphatidylinositol-3-kinase. PKB alpha is a pleiotrophic protein that is involved in a large number of different cellular responses to phosphatidylinositol-3-kinase activation. Coffer et al., 1998, Biochem. J. 335:1–13. These responses include increased expression of FAS ligand and antiapoptotic genes, increased cAMP concentration, increased protein synthesis, and increased glycogen synthesis. VanHaesebroack and Alessi, 2000, Biochem. J. 346:561.

Recently, it has been discovered that over-expression of a PKB alpha gene product in mammalian cell lines grown in tissue culture results in cells that have enhanced properties. For example, such cells were better able to grow and produce recombinant proteins in serum-free, protein-free, and/or peptone-free culture medium. PCT/US00/23483.

As more genes are being identified through genomic techniques, the need to rapidly express recombinant proteins for functional studies has become increasingly acute. In addition, as more protein-based drugs demonstrate clinical effectiveness, the need for increased quantities of such proteins for commercial use increases. At the same time, the building and regulatory approval of culture facilities to address this commercial need takes significant investments in both capital and time. Hence, there is a growing need in the art for the optimization of yields of recombinant protein from cultured cells.

SUMMARY OF THE INVENTION

The invention addresses these needs by identifying and modulating the crucial gene products whose activation or inhibition will increase recombinant protein expression. Specifically, the invention is based, in part, on the discovery that translational regulator gene products that are targets of PKB alpha can be genetically engineered so as to increase recombinant protein expression. These translation regulators include but are not limited to 4E-BP1, mTOR and p70 S6 kinase.

DETAILED DESCRIPTION OF THE INVENTION

Figure 1:
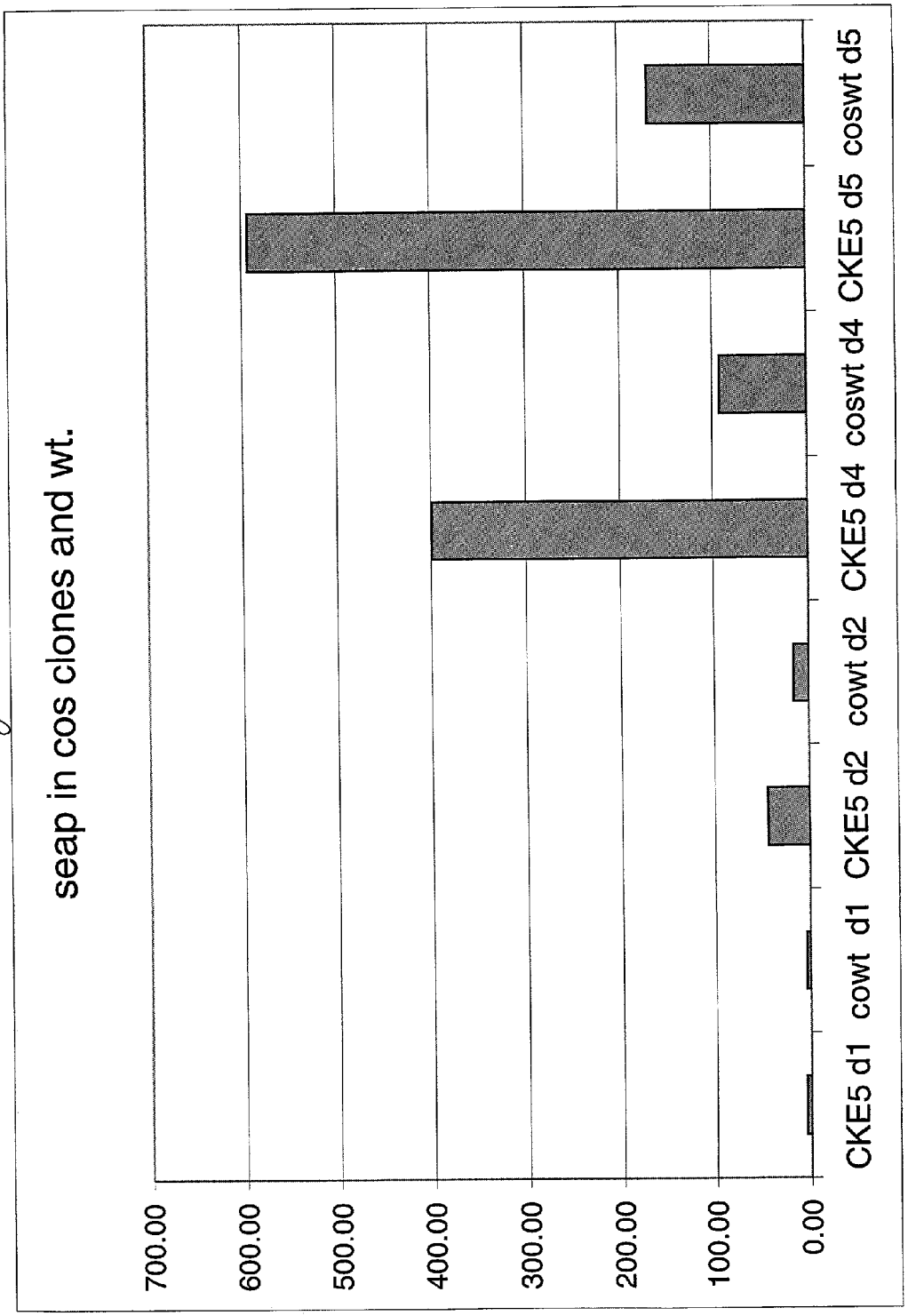
FIG. 1 illustrates the units of SEAP per ml of culture for CKE5 cells (COS-1 stably transformed with the PKB alpha vector and overexpressing this protein) and COSwt cells (COS-1 parental cell line). Cells were grown in adherent culture, and sampled at days 1, 2, 4, and 5 as indicated.

As shown by the experimental data reported herein, cells that stably overproduce PKB alpha will produce significantly higher levels of a recombinant protein of interest. Although PKB alpha is known to be an anti-apoptotic factor, these increases in recombinant protein expression appear in fact to be due to the activation of translational regulator gene products that are downstream targets for PKB alpha. Specifically, transient transfections with an expression plasmid for a gene of interest were performed on two different types of cell lines—one transformed with a PKB alpha expression vector and stably over-expressing PKB alpha, and the parental cell line. Production levels of the gene of interest were greatly increased in the cells that over-express PKB alpha, although viability and mRNA levels were comparable. Thus, PKB alpha acts to stimulate translation of the gene of interest.

Accordingly, altering the regulation of cellular translation downstream of PKB alpha in this pathway can be used to increase the expression of recombinant genes of interest. Cells with advantageous properties are created by genetically engineering cells to activate or inhibit translational regulator gene products. Translational regulator gene products advantageously upregulated in the compositions and methods of the invention are those whose increase in activity stimulate translation, including but are not limited to mTOR and p70 S6 kinase. mTOR is also described as RAFT and FRAP, and is described in Sabatini et al., 1994, Cell 78(1): 35–43, Brown et al., 1994, Nature 369(6483):756–758, and U.S. Pat. No. 6,127,521, incorporated by reference herein. Methods of upregulating a translational regulator gene product include overexpression of the encoded wild-type protein, expression of an altered protein (e.g., partly or constitutively activated mutant, or a protease resistant form), or a genetically engineering the cells to express a protein with an altered cellular distribution (e.g., nucleoplasm) that has increased activity. If overexpression is selected, it should be noted that expression of extremely high levels of any gene product is detrimental or even lethal to a cell, and as such should be avoided. Titration of the appropriate expression level can be manipulated in any of a number of ways (e.g., by choice of promoter or change in gene copy number) and is within the skill of those in the art.

Generally, the cells are genetically engineered to express a translational regulator gene product that is homologous to, or derived from the same species, as that of the cell. However, as many of these gene products tend to be well conserved, it is expected that even expression of heterologous gene products will be advantageous.

Another way of activating translation that is within the scope of the invention is to reduce the activity of translational regulator gene products whose activity inhibits translation. Such translational inhibitors include but are not limited to 4E-BP1 (the sequence of which is described in U.S. Pat. No. 5,874,231, incorporated by reference herein). Methods of downregulating translational regulator gene products include the use of ribozyme technologies, antisense and triple helix technologies, targeted homologous recombination to knockout or otherwise alter the endogenous gene, interfering RNA (RNAi; see, for example, EP 1152056), and expression of dominant negative mutant forms of the gene product. Such methods of upregulating and/or down-regulating the expression of gene products are well known to those of skill in the art.

One way of altering expression of a translational regulator gene product is by placing the sequences encoding it under the control of a heterologous regulatory element. By a "heterologous regulatory element" is meant a genetically encoded element that affects the transcriptional or translational regulation of a coding sequence operably linked thereto, wherein the element is not normally found in nature associated or operatively linked to the coding sequence. Heterologous regulatory elements can be promoters, enhancer regions, transcriptional initiation sites, transcriptional termination signals (e.g., poly adenylation signals), translational initiation sequences, etc. Promoters can be constitutive promoters (e.g., those derived from housekeeping genes whose transcription rate is relatively constant, or some viral promoters), inducible promoters (e.g., the metallothionin promoter that is induced in the presence of heavy metals), tissue or cell type specific promoters (e.g., the globin promoters) or promoters derived from animal viruses (e.g., those from CMV, SV40, Adenoviral, Herpesvirus, RSV, HIV, etc.). Enhancers typically increase the level of transcription from operatively linked genes. Enhancers can also be constitutive, tissue specific, and/or inducible (e.g., the CMV enhancer, the SV40 enhancer, the HIV TAR enhancer). One can also use promoters that are repressible, and silencer elements, to reduce expression of a translational regulator gene product.

Also encompassed within the scope of the invention are cells, the use of such cells, and methods of making such cells, in which any combination of two or more of the above-translational regulator gene products are altered (through activation of translational activators and/or reducing the activity of translational inhibitors). Further encompassed within the scope of the invention is any one or combination of the above-described alterations of translational regulator gene products, in addition to the alteration of expression of one or more IGF-1 signaling pathway genes (described in PCT/US00/23483, incorporated by reference herein) and/or a NF-kappa-B genes. IGF-1 signaling pathway genes that can be altered by upregulation include but are not limited to the IGF-1 receptor (particularly the β subunit), PKBs (PKBα, PKBβ and PKBγ), the MEKs (MEK1 and MEK2), the MAPKs (including p38, p44/ERK1 and p42/ERK2), JNK1, JNK2, JNK3, 14-3—3 protein, IRS-1, IRS-2, BAD, PI3 kinase, PDK1 and PDK2. In addition, upregulation of sugar transporters such as glut1 and glut5 can also be combined with any of the herein described alterations. IGF-1-signaling pathway genes that are advantageously downregulated in the compositions and methods of the invention include PTEN, BAD, gsk3, and phosphatases that dephosphorylate any of the proteins, or their substrates, that are advantageously upregulated. NF-kappa-B genes are members of the conserved family of genes whose subunits form homodimeric and heterodimeric proteins that bind to NF-kappa-B binding sites and positively regulate genes. Generally, NF-kappa-B genes show homology to the rel oncogene. NF-kappa-B genes that are advantageously upregulated in the compositions and methods of the invention include but are not limited to p65, p50, cRe1, p52 and Re1B. Another way of activating NF-kappa-B that is within the scope of the invention is to underexpress or knock out expression of one or more of the family of inhibitor proteins known as IKB. The IKB family consists of IKB-alpha, IKB-beta, IKB-gamma, and other IKB related proteins, such as Bcl–3.

The invention can be used in the production of just about any protein, and is particularly advantageous for proteins whose expression is under the control of a strong promoter, such as for example, a viral promoter. A protein is generally understood to be a polypeptide of at least about 10 amino acids, more preferably at least about 25 amino acids, even more preferably at least about 75 amino acids, and most preferably at least about 100 amino acids.

Generally, the methods of the invention are useful for the production of recombinant proteins. Recombinant proteins are proteins produced by the process of genetic engineering. The term "genetic engineering" refers to a recombinant DNA or RNA method used to create a host cell that expresses a gene at elevated levels, at lowered levels, or a mutant form of the gene. In other words, the cell has been transfected, transformed or transduced with a recombinant polynucleotide molecule, and thereby altered so as to cause the cell to alter expression of a desired protein. Methods and vectors for genetically engineering cells and/or cell lines to express a protein of interest are well known to those skilled in the art; for example, various techniques are illustrated in *Current Protocols in Molecular Biology*, Ausubel et al., eds. (Wiley & Sons, New York, 1988, and quarterly updates) and Sambrook et al., *Molecular Cloning: A Laboratory Manual* (Cold Spring Laboratory Press, 1989). Genetic engineering techniques include but are not limited to expression vectors, targeted homologous recombination and gene activation (see, for example, U.S. Pat. No. 5,272,071 to Chappel) and trans activation by engineered transcription factors (see, for example, Segal et al., 1999, Proc. Natl. Acad. Sci. USA 96(6):2758–63). Preferably, the proteins are expressed under the control of a heterologous control element such as, for example, a promoter that does not in nature direct the production of that protein. For example, the promoter can be a strong viral promoter (e.g., CMV, SV40) that directs the expression of a mammalian protein. The host cell may or may not normally produce the protein. For example, the host cell can be a CHO cell that has been genetically engineered to produce a human protein. Alternatively, the host cell can be a human cell that has been genetically engineered to produce increased levels of a human protein normally present only at very low levels (e.g., by replacing the endogenous promoter with a strong viral promoter).

The proteins can be produced recombinantly in eukaryotic cells and are preferably secreted by host cells adapted to grow in cell culture. Host cells for use in the invention are preferably mammalian cells. Preferably, the cells are also genetically engineered to express a gene of interest. Even more preferably, the host cells are mammalian production cells adapted to grow in cell culture. Examples of such cells commonly used in the industry are CHO, VERO, BHK, HeLa, CV1 (including Cos cells, as illustrated below by way of example), MDCK, 293, 3T3, myeloma cell lines (especially murine), PC12 and WI38 cells. For example, host cells can be Chinese hamster ovary (CHO) cells, which are widely used for the production of several complex recombinant proteins, e.g. cytokines, clotting factors, and antibodies (Brasel et al., 1996, Blood 88:2004–2012; Kaufman et al., 1988, J. Biol Chem 263: 6352–6362; McKinnon et al., 1991, J Mol Endocrinol 6:231–239; Wood et al., 1990, J. Immunol 145:3011–3016). The dihydrofolate reductase (DHFR)-deficient mutant cell line (Urlaub et al., 1980, Proc Natl Acad Sci USA 77:4216–4220), DXB11 and DG-44, are the CHO host cell lines of choice because the efficient DHFR selectable and amplifiable gene expression system allows high level recombinant protein expression in these cells (Kaufman R. J., 1990, Meth Enzymol 185:527–566). In addition, these cells are easy to manipulate as adherent or suspension cultures and exhibit relatively good genetic stability. CHO cells and recombinant proteins expressed in them have been extensively characterized and have been approved for use in clinical manufacturing by regulatory agencies.

The invention can be used for both transiently- and stably-transfected cells. The term "transiently-transfected" is used in reference to an expression construct, and refers to cells that contain that expression construct, but have not been selected for stable integration of that construct into their genome or nucleus of the expression construct. Thus, "stably-transfected" cells are cells that have been selected for stable integration of the expression construct.

Various tissue culture media, including serum-free and/or defined culture media, are commercially available for cell culture. Tissue culture media is defined, for purposes of the invention, as a media suitable for growth of animal cells, and preferably mammalian cells, in in vitro cell culture. Typically, tissue culture media contains a buffer, salts, energy source, amino acids, vitamins and trace essential elements. Any media capable of supporting growth of the appropriate eukaryotic cell in culture can be used; the invention is broadly applicable to eukaryotic cells in culture, particularly mammalian cells, and the choice of media is not crucial to the invention. Tissue culture media suitable for use in the invention are commercially available from, e.g., ATCC (Manassas, Va.). For example, any one or combination of the following media can be used: RPMI-1640 Medium, Dulbecco's Modified Eagle's Medium, Minimum Essential Medium Eagle, F-12K Medium, Iscove's Modified Dulbecco's Medium. When defined medium that is serum-free and/or peptone-free is used, the medium is usually highly enriched for amino acids and trace elements (see, for example, U.S. Pat. No. 5,122,469 to Mather et al., and U.S. Pat. No. 5,633,162 to Keen et al.).

In the methods and compositions of the invention, cells can be grown in serum-free, protein-free, growth factor-free, and/or peptone-free media. The term "serum-free" as applied to media includes any mammalian cell culture medium that does not contain serum, such as fetal bovine serum. The term "insulin-free" as applied to media includes any medium to which no exogenous insulin has been added. By exogenous is meant, in this context, other than that produced by the culturing of the cells themselves. The term "IGF-1-free" as applied to media includes any medium to which no exogenous Insulin-like growth factor-1 (IGF-1) or analog (such as, for example, LongR$^3$-IGF-1, see below) has been added. The term "growth-factor free" as applied to media includes any medium to which no exogenous growth factor (e.g., insulin, IGF-1) has been added. The term "protein-free" as applied to media includes medium free from exogenously added protein, such as, for example, transferrin and the protein growth factors IGF-1 and insulin. Protein-free media may or may not have peptones. The term "peptone-free" as applied to media includes any medium to which no exogenous protein hydrolysates have been added such as, for example, animal and/or plant protein hydrolysates. Peptone-free media has the advantages of lower lot to lot variability and fewer filtration problems than media containing plant or animal hydrolysates. Chemically defined media are media in which every component is defined and obtained from a pure source, preferably a non-animal source.

Particularly preferred proteins of interest for expression using the invention are protein-based drugs, also known as biologics. Preferably, the proteins of interest are expressed as extracellular products. Proteins that can be produced using the methods of the invention include but are not limited to a Flt3 ligand, a CD40 ligand, erythropoeitin, thrombopoeitin, calcitonin, Fas ligand, ligand for receptor activator of NF-kappa B (RANKL), TNF-related apoptosis-inducing ligand (TRAIL), ORK/Tek, thymic stroma-derived lymphopoietin, granulocyte colony stimulating factor, granulocyte-macrophage colony stimulating factor, mast cell growth factor, stem cell growth factor, epidermal growth factor, RANTES, growth hormone, insulin, insulinotropin, insulin-like growth factors, parathyroid hormone, interferons, nerve growth factors, glucagon, interleukins 1 through 18, colony stimulating factors, lymphotoxin-β, tumor necrosis factor, leukemia inhibitory factor, oncostatin-M, and various ligands for cell surface molecules Elk and Hek (such as the ligands for eph-related kinases, or LERKS). Descriptions of proteins that can be produced according to the inventive methods may be found in, for example, *Human Cytokines: Handbook for Basic and Clinical Research, Vol. II* (Aggarwal and Gutterman, eds. Blackwell Sciences, Cambridge Mass., 1998); *Growth Factors: A Practical Approach* (McKay and Leigh, eds., Oxford University Press Inc., New York, 1993) and *The Cytokine Handbook* (A W Thompson, ed.; Academic Press, San Diego Calif.; 1991).

Production of the receptors for any of the aforementioned proteins can also be improved using the inventive methods, including the receptors for both forms of tumor necrosis factor receptor (referred to as p55 and p75), Interleukin-1 receptors (type 1 and 2), Interleukin-4 receptor, Interleukin-15 receptor, Interleukin-17 receptor, Interleukin-18 receptor, granulocyte-macrophage colony stimulating factor receptor, granulocyte colony stimulating factor receptor, receptors for oncostatin-M and leukemia inhibitory factor, receptor activator of NF-kappa B (RANK), receptors for TRAIL, and receptors that comprise death domains, such as Fas or Apoptosis-Inducing Receptor (AIR). A particularly preferred receptor is a soluble form of the IL-1 receptor type II; such proteins are described in U.S. Pat. No. 5,767,064, incorporated herein by reference in its entirety.

Other proteins that can be produced using the inventive methods include cluster of differentiation antigens (referred to as CD proteins), for example, those disclosed in *Leukocyte Typing VI* (*Proceedings of the VIth International Workshop and Conference*; Kishimoto, Kikutani et al., eds.; Kobe, Japan, 1996), or CD molecules disclosed in subsequent workshops. Examples of such molecules include CD27, CD30, CD39, CD40; and ligands thereto (CD27 ligand, CD30 ligand and CD40 ligand). Several of these are members of the TNF receptor family, which also includes 41BB and OX40; the ligands are often members of the TNF family (as are 41BB ligand and OX40 ligand); accordingly, members of the TNF and TNFR families can also be produced using the present invention.

Proteins that are enzymatically active can also be produced according to the instant invention. Examples include metalloproteinase-disintegrin family members, various kinases, glucocerebrosidase, superoxide dismutase, tissue plasminogen activator, Factor VIII, Factor IX, apolipoprotein E, apolipoprotein A-I, globins, an IL-2 antagonist, alpha-1 antitrypsin, TNF-alpha Converting Enzyme, and numerous other enzymes. Ligands for enzymatically active proteins can also be produced by applying the instant invention.

The inventive compositions and methods are also useful for production of other types of recombinant proteins, including immunoglobulin molecules or portions thereof, and chimeric antibodies (i.e., an antibody having a human constant region couples to a murine antigen binding region) or fragments thereof. Numerous techniques are known by which DNA encoding immunoglobulin molecules can be manipulated to yield DNAs capable of encoding recombinant proteins such as single chain antibodies, antibodies with enhanced affinity, or other antibody-based polypeptides (see, for example, Larrick et al., 1989, Biotechnology 7:934–938; Reichmann et al., 1988, Nature 332:323–327; Roberts et al., 1987, Nature 328:731–734; Verhoeyen et al., 1988, Science 239:1534–1536; Chaudhary et al., 1989, Nature 339:394–397). Recombinant cells producing fully human antibodies (such as are prepared using transgenic animals, and optionally further modified in vitro), as well as humanized antibodies, can also be used in the invention. The term humanized antibody also encompasses single chain antibodies. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0 451 216 B1; and Padlan, E. A. et al., EP 0 519 596 A1. For example, the invention can be used to induce the expression of human and/or humanized antibodies that immunospecifically recognize specific cellular targets, e.g., the human EGF receptor, the her-2/neu antigen, the CEA antigen, Prostate Specific Membrane Antigen (PSMA), CD5, CD11a, CD18, NGF, CD20, CD45, Ep-cam, other cancer cell surface molecules, TNF-alpha, TGF-b1, VEGF, other cytokines, alpha 4 beta 7 integrin, IgEs, viral proteins (for example, cytomegalovirus), etc., to name just a few.

Various fusion proteins can also be produced using the inventive methods. A fusion protein is a protein, or domain or a protein (e.g. a soluble extracellular domain) fused to a heterologous protein or peptide. Examples of such fusion proteins include proteins expressed as a fusion with a portion of an immunoglobulin molecule, proteins expressed as fusion proteins with a zipper moiety, and novel polyfunctional proteins such as a fusion proteins of a cytokine and a growth factor (i.e., GM-CSF and IL-3, MGF and IL-3). WO 93/08207 and WO 96/40918 describe the preparation of various soluble oligomeric forms of a molecule referred to as CD40L, including an immunoglobulin fusion protein and a zipper fusion protein, respectively; the techniques discussed therein are applicable to other proteins. Any of the above molecules can be expressed as a fusion protein including but not limited to the extracellular domain of a cellular receptor molecule, an enzyme, a hormone, a cytokine, a portion of an immunoglobulin molecule, a zipper domain, and an epitope.

After induction using the methods of the invention, the resulting expressed protein can then be collected. In addition the protein can purified, or partially purified, from such culture or component (e.g., from culture medium or cell extracts or bodily fluid) using known processes. By "partially purified" means that some fractionation procedure, or procedures, have been carried out, but that more polypeptide species (at least 10%) than the desired protein is present. By "purified" is meant that the protein is essentially homogeneous, i.e., less than 1% contaminating proteins are present. Fractionation procedures can include but are not limited to one or more steps of filtration, centrifugation, precipitation, phase separation, affinity purification, gel filtration, ion exchange chromatography, hydrophobic interaction chromatography (HIC; using such resins as phenyl ether, butyl ether, or propyl ether), HPLC, or some combination of above.

For example, the purification of the polypeptide can include an affinity column containing agents which will bind to the polypeptide; one or more column steps over such affinity resins as concanavalin A-agarose, heparin-toyopearl® or Cibacrom blue 3GA Sepharose®; one or more steps involving elution; and/or immunoaffinity chromatography. The polypeptide can be expressed in a form that facilitates purification. For example, it may be expressed as a fusion polypeptide, such as those of maltose binding polypeptide (MBP), glutathione-S-transferase (GST) or thioredoxin (TRX). Kits for expression and purification of such fusion polypeptides are commercially available from New England BioLab (Beverly, Mass.), Pharmacia (Piscataway, N.J.) and InVitrogen, respectively. The polypeptide can be tagged with an epitope and subsequently purified by using a specific antibody directed to such epitope. One such epitope (FLAG®) is commercially available from Kodak (New Haven, Conn.). It is also possible to utilize an affinity column comprising a polypeptide-binding polypeptide, such as a monoclonal antibody to the recombinant protein, to affinity-purify expressed polypeptides. Other types of affinity purification steps can be a Protein A or a Protein G column, which affinity agents bind to proteins that contain Fc domains. Polypeptides can be removed from an affinity column using conventional techniques, e.g., in a high salt elution buffer and then dialyzed into a lower salt buffer for use or by changing pH or other components depending on the affinity matrix utilized, or can be competitively removed using the naturally occurring substrate of the affinity moiety.

The desired degree of final purity depends on the intended use of the polypeptide. A relatively high degree of purity is desired when the polypeptide is to be administered in vivo, for example. In such a case, the polypeptides are purified such that no polypeptide bands corresponding to other polypeptides are detectable upon analysis by SDS-polyacrylamide gel electrophoresis (SDS-PAGE). It will be recognized by one skilled in the pertinent field that multiple bands corresponding to the polypeptide can be visualized by SDS-PAGE, due to differential glycosylation, differential post-translational processing, and the like. Most preferably, the polypeptide of the invention is purified to substantial homogeneity, as indicated by a single polypeptide band upon analysis by SDS-PAGE. The polypeptide band can be visualized by silver staining, Coomassie blue staining, or (if the polypeptide is radiolabeled) by autoradiography.

The invention also optionally encompasses further formulating the proteins. By the term "formulating" is meant that the proteins can be buffer exchanged, sterilized, bulk-packaged and/or packaged for a final user. For purposes of the invention, the term "sterile bulk form" means that a formulation is free, or essentially free, of microbial contamination (to such an extent as is acceptable for food and/or drug purposes), and is of defined composition and concentration. The term "sterile unit dose form" means a form that is appropriate for the customer and/or patient administration or consumption. Such compositions can comprise an effective amount of the protein, in combination with other components such as a physiologically acceptable diluent, carrier, or excipient. The term "physiologically acceptable" means a non-toxic material that does not interfere with the effectiveness of the biological activity of the active ingredient(s).

Formulations suitable for administration include aqueous and non-aqueous sterile injection solutions which may contain anti-oxidants, buffers, bacteriostats and solutes which render the formulation isotonic with the blood of the recipient; and aqueous and non-aqueous sterile suspensions which may include suspending agents or thickening agents. The polypeptides can be formulated according to known methods used to prepare pharmaceutically useful compositions. They can be combined in admixture, either as the sole active material or with other known active materials suitable for a given indication, with pharmaceutically acceptable diluents (e.g., saline, Tris-HCl, acetate, and phosphate buffered solutions), preservatives (e.g., thimerosal, benzyl alcohol, parabens), emulsifiers, solubilizers, adjuvants and/or carriers. Suitable formulations for pharmaceutical compositions include those described in *Remington's Pharmaceutical Sciences,* 16th ed. 1980, Mack Publishing Company, Easton, Pa. In addition, such compositions can be complexed with polyethylene glycol (PEG), metal ions, or incorporated into polymeric compounds such as polyacetic acid, polyglycolic acid, hydrogels, dextran, etc., or incorporated into liposomes, microemulsions, micelles, unilamellar or multilamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323. Such compositions will influence the physical state, solubility, stability, rate of in vivo release, and rate of in vivo clearance, and are thus chosen according to the intended application, so that the characteristics of the carrier will depend on the selected route of administration. Sustained-release forms suitable for use include, but are not limited to, polypeptides that are encapsulated in a slowly-dissolving biocompatible polymer (such as the alginate microparticles described in U.S. Pat. No. 6,036,978), admixed with such a polymer (including topically applied hydrogels), and or encased in a biocompatible semi-permeable implant.

The invention having been described, the following examples are offered by way of illustration, and not limitation.

EXAMPLE 1

Over-Expression of PKB Alpha Improves Recombinant Protein Expression in a Transient System The effect of over-expressing PKB was examined in COS 1 cells. COS 1 cells were stably transformed with pcDNA-PKB alpha (hamster) as described in PCT/US00/23483. Clonal cell lines of the transformed COS1 cells were then supertransfected with an expression plasmid that directed expression of a recombinant protein, SEAP, as a reporter gene, under the control of an SV40 promoter/enhancer. The parental cell line was also transfected with the expression plasmid.

The COS-1 cells were grown in Dulbecco's Modified Eagles Medium/F12, with the addition of 1% penicillin streptomycin (100× stock, GibcoBRL, Grand Island, N.Y.), 1% Glutamax (GibcoBRL), and 5% fetal bovine serum (FBS) (Hyclone, Logan, Vt.). Cells were grown adherently in culture dishes for up to 5 days. Samples of medium (for protein analysis), and/or cells (for RNA analysis), were taken on the days indicated. Viability was determined by Alamar Blue assay.

Total cellular RNA was isolated using an Rneasy Kit and Qiashredder (Qiagen, Valencia, Calif.) and quantitated using RT-PCR. A PTC 200DNA engine from MJ Research was used for RT reactions, and PCR was performed using the Cyber Green PCR mix, a GENE Amp5700 instrument, and protocols provided by Applied Biosystems (Foster City, Calif.). SEAP was assayed using standard commercial assay kits.

Production of the recombinant protein SEAP was examined in the two types of transiently transfected cells. FIG. 1 illustrates the units of SEAP per ml of each culture at days 1, 2, 4, and 5. From day 2 onwards, it can be seen that SEAP production was greatly improved in the CKE5 cells (stably transformed with the PKB alpha vector and overexpressing this protein) compared to the COSwt cells (parental cell line). The mechanism for this increase in expression of the product of the gene of interest was further investigated. Although PKB alpha is thought to have anti-apoptotic activity that could conceivably have accounted for the difference in production, cell viability over the course of the experiment, as measured by a standard Alamar blue assay, was comparable between the two transfected pools. Thus, the observed difference in production could not be attributed to a difference in cell survival.

Also investigated was a metabolic difference between the two cell lines. It has been reported that PKB alpha is involved in translocation of GLUT-4 from the cytoplasm to the cell membrane. Since GLUT-4 plays an active role in transport of glucose, the uptake of glucose and the production of lactate in production cultures was measured. Experiments were performed in both serum-free and serum-containing media with several reporters. Glucose and lactate levels in the media were measured daily up to 14 days post-transfection. In all instances no significant difference between the cell lines was observed in the lactate produced or glucose consumed.

Figure 2:
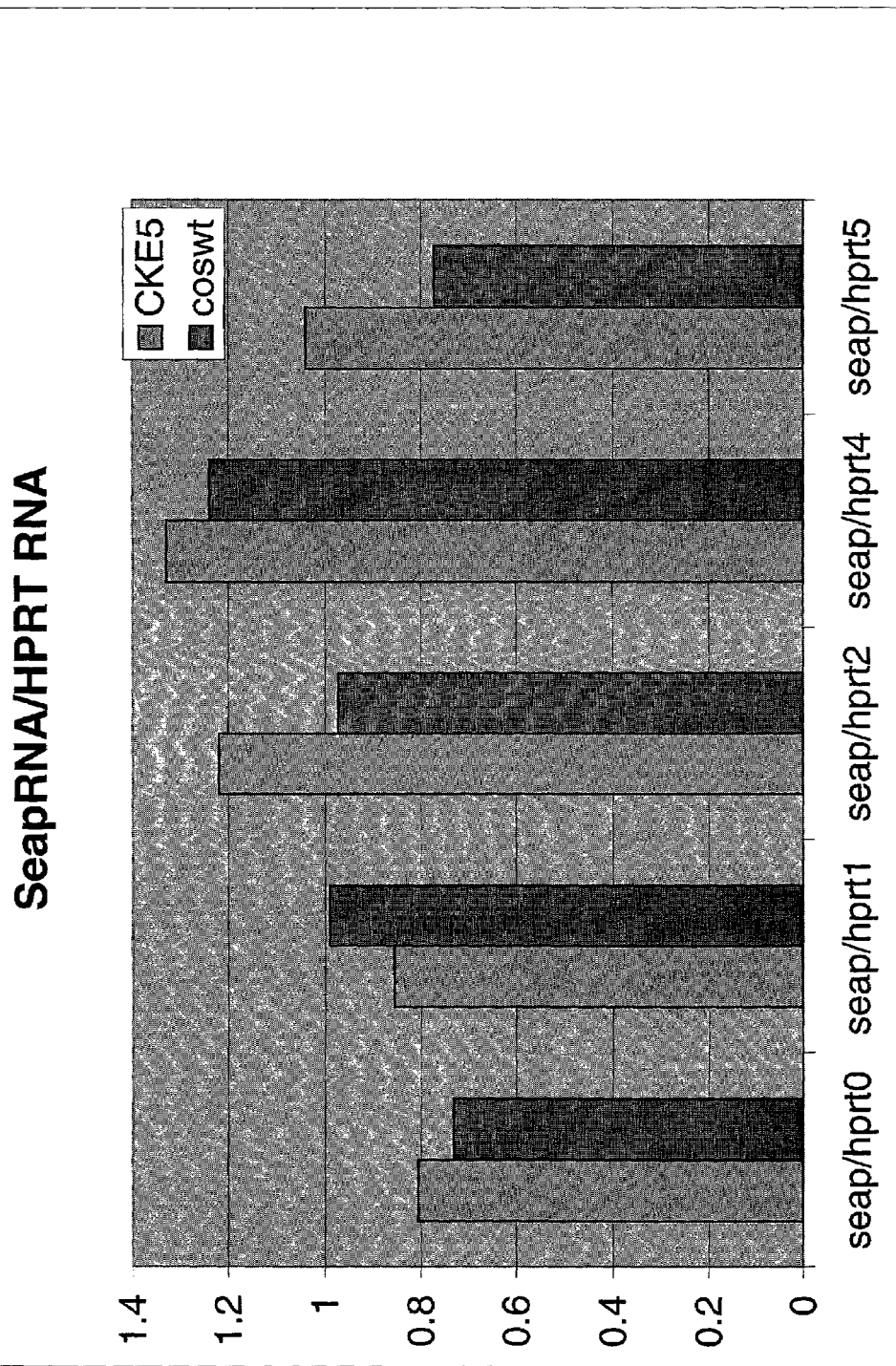
FIG. 2 illustrates the amount of SEAP mRNA as a function of HPRT mRNA in CKE5 cells (COS-1 stably transformed with the PKB alpha vector and overexpressing this protein) and COSwt cells. Total cellular RNA was isolated and assayed using RT-PCR at days 0, 1, 2, 4, and 5, as indicated.

Message levels for the SEAP mRNA were then assayed using quantitative RT-PCR. The results are depicted in FIG. 2. The message for HPRT mRNA was used as an internal control for the levels of SEAP mRNA. There was no significant difference in transfection efficiency. The amount of SEAP mRNA per cell did not significantly differ, and therefore could not account for the production difference in protein between the CKE5 and COSwt cells. Accordingly, translation of the mRNA encoding for the SEAP reporter was higher in the cells stably overexpressing PKB alpha. Since one of the many different effects of PKB alpha is on translational control, these data indicate that activation of translation was occurring in the cells stably overexpressing PKB alpha. Thus, regulation of the downstream targets of PKB alpha will enhance recombinant protein production in cell culture. These targets include but are not limited mTOR, p70 S6 kinase, and 4E-BP1 (Aoki et al., 2001, PNAS 98:136–141; Dufner et al., 1999, Mol. Cell. Biol. 19:4525–4534).

EXAMPLE 2

Examination of p70 S6 Kinase Phosphorylation Status in Cells that Overexpress PKB Alpha Western blot analysis was performed to detect the presence of phosphorylated S6 kinase in the parental COS-1 cell line, and in the COS-1 clones (CKE5 and CKA9) that overexpress PKB alpha. Cells were starved for 4 hours in serum-free media and then either remained untreated, or were treated by the addition of 20% serum for 30 minutes.

Cells were washed with PBS and lysed in cell lysis buffer (Cell Signaling Technology, Beverly, Mass., catalog no. 9803). Lysates from equal numbers of cells were separated by electrophoresis using 4–12% Bis-Tris gels (Novex/Invitrogen, Carlsbad, Calif.) under conditions recommended by the supplier. After running the gel, proteins were transferred to nitrocellulose, and Western blotted with Phospho-p70 S6 kinase (Thr389) antibody (Cell Signaling Technology) as a primary antibody to detect phosphorylated S6 kinase. HRP conjugated Goat anti Rabbit was used as a secondary antibody, and the primary:secondary antibody complex was then detected with the enhanced chemiluminescence assay (ECL; Amersham, Piscataway, N.J.). Cell extracts from NIH-3T3 (Cell Signaling Technology) were used as positive and negative controls. Significant phosphorylation of S6 kinase at Thr389 was detected only in lane 2, from the cell extracts formed from NIH-3T3 cells treated with serum (Cell Signaling Technology). When the extracts were analyzed with antibody to p70 S6 kinase, the protein was visualized in all lanes. Based on this result, overexpression of PKB alpha did not result in any significant change in phosphorylation of p70 S6 kinase that could be detected with these antibodies.

| Lane | Sample | Presence of p70 S6 kinase | Detection of Phosphorylated p70 S6 kinase |
|---|---|---|---|
| 1 | NIH-3T3 −serum | +++ | + |
| 2 | NIH-3T3 +serum | +++ | +++ |
| 3 | CKA9 −serum | +++ | + |
| 4 | CKA9 +serum | +++ | + |
| 5 | CKE5 −serum | +++ | + |
| 6 | CKE5 +serum | +++ | + |
| 7 | COS-1 −serum | +++ | + |
| 8 | COS-1 +serum | +++ | + |

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. An isolated eukaryotic host cell genetically engineered to express a protein of interest wherein the protein of interest is expressed as an extracellular product and wherein the eukaryotic cell has been genetically engineered to also express mammalian Target of Rapamycin (mTOR).

2. The eukaryotic host cell of claim 1 wherein the host cell is further genetically engineered to express a first selectable marker.

3. The eukaryotic host cell of claim 1 wherein the host cell is a mammalian cell.

4. The eukaryotic host cell of claim 3 wherein the host cell is selected from the group consisting of CHO, VERO, BHK, HeLa, CV1, COS, MDCK, 293, 3T3, myeloma, PC12 and WI38 cells.

5. The eukaryotic host cell of claim 1 wherein the host cell is adapted to grow in serum-free medium.

6. The eukaryotic host cell of claim 5 wherein the host cell is adapted to grow in protein-free medium.

7. The eukaryotic host cell of claim 1 wherein the protein of interest is selected from the group consisting of a soluble TNF receptor, a soluble IL-4 receptor, a soluble IL-1 type II receptor, a soluble Flt3 ligand, a soluble CD40 ligand, CD39, CD30, CD27, a TEK/Ork, IL-15, a soluble IL-15 receptor, Ox 40, GM-CSF, RANKL, RANK, TRAIL, a soluble TRAIL receptor, tissue plasminogen activator, Factor VIII, Factor IX, apolipoprotein E, apolipoprotein A-I, an IL-2 receptor, an IL-2 antagonist, alpha-1 antitrypsin, calcitonin, growth hormone, insulin, insulinotropin, insulin-like growth factors, parathyroid hormone, interferons, superoxide dismutase, glucagon, an erythropoeitin, an antibody, glucocerebrosidase, an Fc-fusion protein, globins, nerve growth factors, interleukins, and colony stimulating factors.

8. A method of producing a protein of interest, the method comprising culturing an isolated eukaryotic host cell genetically engineered to express a protein of interest wherein the protein of interest is an extracellular product and wherein the host cell is genetically engineered to also express mTOR, under conditions such that the protein of interest is expressed.

9. The method of claim 8 further comprising collecting the protein of interest.

10. The method of claim 8 wherein the eukaryotic host cell is transiently transfected.

11. The method of claim 8 wherein the eukaryotic host cell is stably transformed.

12. The method of claim 8 wherein the eukaryotic host cell is selected from the group consisting of CHO, VERO, BHK, HeLa, CV1, COS, MDCK, 293, 3T3, myeloma, PC12 and WI38 cells.

13. The method of claim 8 wherein the protein of interest is selected from the group consisting of a soluble TNF receptor, a soluble IL-4 receptor, a soluble IL-1 type II receptor, a soluble Flt3 ligand, a soluble CD40 ligand, CD39, CD30, CD27, a TEK/Ork, IL-15, a soluble IL-15 receptor, Ox 40, GM-CSF, RANKL, RANK, TRAIL, a soluble TRAIL receptor, tissue plasminogen activator, Factor VIII, Factor IX, apolipoprotein E, apolipoprotein A-I, an IL-2 receptor, an IL-2 antagonist, alpha-1 antitrypsin, calcitonin, growth hormone, insulin, insulinotropin, insulin-like growth factors, parathyroid hormone, interferons, superoxide dismutase, glucagon, an erythropoeitin, an antibody, glucocerebrosidase, an Fc-fusion protein, globins, nerve growth factors, interleukins, and colony stimulating factors.

14. The method of claim 8 wherein the eukaryotic host cell is adapted to grow in serum-free medium.

* * * * *